United States Patent [19]
Plunkett et al.

[11] Patent Number: 5,382,427
[45] Date of Patent: Jan. 17, 1995

[54] USE OF IL-4 TO TREAT SOLID TUMORS

[75] Inventors: Marian L. Plunkett, Edison; Joseph J. Catino, Lebanon, both of N.J.

[73] Assignee: Schering-Plough Corporation, Kenilworth, N.J.

[21] Appl. No.: 984,414

[22] PCT Filed: Sep. 3, 1991

[86] PCT No.: PCT/US91/06126
§ 371 Date: Mar. 4, 1993
§ 102(e) Date: Mar. 4, 1993

[87] PCT Pub. No.: WO92/04044
PCT Pub. Date: Mar. 19, 1992

Related U.S. Application Data

[63] Continuation-in-part of Ser. No. 578,968, Sep. 6, 1990, abandoned.

[51] Int. Cl.⁶ .................... A61K 37/02; C07K 13/00
[52] U.S. Cl. ............................ 424/85.2; 424/85.1
[58] Field of Search ............................ 424/85.1, 85.2

[56] References Cited

U.S. PATENT DOCUMENTS
4,958,007 9/1990 Alroy et al. .................... 530/351

FOREIGN PATENT DOCUMENTS
0302429 8/1988 European Pat. Off. .
0342892 11/1989 European Pat. Off. .

OTHER PUBLICATIONS

Tepper et al Murine IL-4 displays potent anti-tumor activity in vivo. Cell 57:503-512 (1989).
Drasa et al J. Immunol. 135:2518-2523 (1985).
Dialog Accession No. 03845880—(Meeting Abstract) Forni, G et al., *Lymphokine Res.* (1990) vol. 9(4), p. 571.
Dialog Accession No. 03803318—Li, W Q et al., (1990) *Mol. Immunol.*, vol. 27(12): pp. 1331-1337 (Abstract only).
Dialog Accession No. 00717021—Forni, G. et al., (Meeting Abstract) Sixth NCT-EORTC Symposium on New Drugs on Cancer Therapy Mar. 7-10 1989 (Amsterdam).
Dialog Accession No. 00765557.—Forni, G. et al. (1989) *Int'l. J. Cancer*, Suppl., vol. 4, pp. 62-65 (Abstract only).
Dialog Accession No. 00711531—Bosco, M. C. et al. (1988) *G Batteriol Virol Immunol.*, vol. 81(1-12) pp. 3-9 (Abstract).
Dialog Accession No. 00693948—Kawakami, Y. et al. (1988) *J. Exp Med.*, vol. 168(6): pp. 2183-2191 (Abstract only).
Bosco, et al., Giorn. Batt. Virol. Immun., vol. LXXXI (1988) pp. 3-9.

*Primary Examiner*—Michael G. Wityshyn
*Assistant Examiner*—C. Sayala
*Attorney, Agent, or Firm*—Thomas D. Hoffman

[57] ABSTRACT

A method of using IL-4, the use of IL-4 for the manufacture of a medicament and pharmaceutical compositions containing IL-4, for treating solid tumor growth by systemically injecting IL-4, such as hIL-4 or recombinant *E. coli*—derived IL-4, into mammals afflicted with solid tumors is disclosed.

9 Claims, 5 Drawing Sheets

USE OF IL-4 TO TREAT SOLID TUMORS

CROSS-REFERENCE TO RELATED APPLICATIONS

This application claims priority of Internal application No.: PCT/US91/06126, having an International filing date of 03 September, 1991, now U.S. Pat. No. WO 9,204,044, and of U.S. Ser. No. 07/578,968, filed Sep. 6, 1990, now abandoned, of which the above-listed International application is a continuation-in-part.

BACKGROUND OF THE INVENTION

This invention relates to methods of using interleukin-4 ("IL-4"), the use of IL-4 for making medicaments, and pharmaceutical compositions containing IL-4, for treating solid tumors in mammals afflicted with solid tumors by systemically administering to said mammals an effective amount of IL-4.

INTRODUCTION

Interleukin-4 [hereinafter "IL-4" but also known as B Cell Stimulatory Factor 1, (BSF-1)]was originally described by M. Howard et al. in *J. Exp. Med.* (1982), Vol. 155, pp. 914–23 as a T cell-derived growth factor, distinct from IL-2, which permitted long-term tissue culture of normal mouse B lymphocytes and which interacted with activated B lymphocytes to maintain the proliferation thereof for as long as 4 months. Although mixed B lymphocyte explants have been used to initiate cultures, it appears that B lymphocytes with immature phenotype are specifically enhanced by IL-4 in tissue culture. See for example C. Perchel et al., *J. Immunol.* (1989), Vol. 142, 1558–1568. In addition, G. Trenn et al. *J. Immunol,* (1988) Vol. 140, 1101–1106 discloses that IL-4 stimulates the development of cytotoxic T cells from the Lyt-2+ subpopulation of resting murine T lymphocytes.

The mouse IL-4 gene was cloned and expressed in COS-7 cells [See T. Otsuka et al., *Nuc. Acids Res.* (1987), Vol. 15, 333–334]. The cloned factor had all the activities in tissue culture seen for the factor purified from T cell culture supernatants. Cloning and expression of the human IL-4 gene have been described by N. Arai et al., *J. Immunol.* (1989), Vol. 142, 274–282 and T. Yokota et al., *Proc. Nat. Acad. Sci.* (1986), Vol. 83, 5844–5848 with the factor produced in COS-7 cells having similar activities to the native molecule as studied in tissue culture. As IL-4 was studied both in human and murine cell systems, additional in-vitro activities were attributed to the molecule: i) IL-4 plays an important role in the induction and regulation of IgE synthesis, a process occuring as B lymphocyte subpopulations are induced into proliferation [See S. Romagnani et el., *Clin. Immunol. Immunopathol* (1989,) Vol. 50, 513–523]; ii) IL-4 induces low affinity Fcε receptors (CD23) on normal human B lymphocytes in tissue culture [See T. DeFrance et el., *J. Exp. Med.* (1987), Vol. 165, 1459–1457]; iii) IL-4 interacts in an extremely precise way with other lymphokines, notably interferon-γ,[See R. L. Coffman et al., *Immunol,* Res. (1988), Vol. 102, 5–27 and S. Romagnani et al., supra]and T cells [See R. L. Coffman et el. supra, S. Romagnani et el. supra, and M. D. Widmer et el., *Nature,* (1987), Vol. 326, 795–98-]to bring about B cell proliferation and alteration; and (iv) IL-4 increases class 11 1 a antigent expression on resting B cells (R Noelle et el., PNAS 81.6149–6153,1984). T. R. Mosmann et el. in *J. Immuno.,* Vol. 138, 1813–1816 disclose that human and murine I-4 which are 50% homologous at amino acid sequence 1–90 and 129–149 are species specific.

Studies in humans showed that IL-4 has an affect on monoclonal B cell tumors. S. Karray et el. in *J. Exp. Med.* (1988) Vol. 168, 85–94, disclose that human IL-4 suppresses the IL-2-dependent proliferation of B-type chronic lymphocytic leukemia (B-CLL) in vitro. C. M. Higuchi et el. in *Can. Res.* (1989) Vol. 49:6487–6492, disclose that in human peripheral blood lymphocytes preactivated by IL-2, IL-4 induces lymphokine-activated killer activity (LAK). J. J. Mule et al. in *J. Exp. Med.,* (1987) Vol. 166; 792–797, disclose that in the murine system, resting splenocytes treated with murine IL-4 alone or in combination with IL-2 generate LAK activity against fresh syngenic tumor cells in vitro. G. Forni et al. in *Int. J. Can. Sup.,* (1989) Vol. 4, 62–65, disclose that antitumor activity can be induced by injecting murine IL-4 around the tumor draining lymph node and that when IL-4 is used in combination with a nonapeptide from human IL-1$\beta$, very active lymphokine-activated tumor inhibition (LATI)is observed. J. J. Mule et al. in *J. Immuno.,* (1984) Vol. 142, 726–733 disclose that the major phenotype of the cells induced by murine IL-4 is surface expression of asialo-GM$_1$, Thy+, Lyt$^2$+, T$^3$+ and that in LAK cells generated by a combination of IL-2 plus IL-4, there is an increase in granule-associated serine esterase. D. J. Peace et al. in *J. Immuno.,* (1988) Vol. 140, 3679–3685 disclose that IL-4 induced LAK activity is associated with two different cell types, one NK-like (NK 1.1+, Lyt2−) and the other T cells like (NK 1.1−, Lyt2+). R. I. Tepper et al. in *Cell,* (May 5, 1989) Vol. 57, 503–512 disclose that murine tumor cell lines transfected with murine IL-4 are inhibited from growing in vivo but that IL-4 transfected tumor cells mixed with nontransfected tumor cells resulted in the inhibition of the nontransfected tumor growth in vivo when the two tumor cell types were colocalized. R. I. Tepper et al. also disclose that when the nontransfected tumor was at a distal site from the IL-4-transfected tumor, inhibition was not observed. R. I. Tepper further disclose that parenteral administration of a cytokine, e.g. IL-2 or IL-4 to a tumor-bearing animal is "compromised by the short half life of the factor (as is the case for IL-2) and the need to obtain the cytokine in quantities sufficient to achieve effective dose levels. G. D'Orazi et al. in Proceedings of the American Association for Cancer Research, (March 1990) Vol. 31 p 252. Abstract No 1490 disclose that IL-4 induced an antitumor response in a nude mice model.

Thus, none of the references of which we are aware disclose whether systemic administration of IL-4 into mammals afflicted with solid tumors would be clinically efficacious in human beings nor does the available in vitro or vivo data predict a systemic anti tumor effect for IL-4 administered to such mammals.

SUMMARY OF THE INVENTION

Surprisingly, we have found that a broad array of solid tumors may be treated by systemically injecting an effective amount of IL-4 into mammals, such as human beings, afflicted with solid tumors at a site distal from the solid tumors.

Accordingly, the present invention provides a method of treating solid tumors in a mammal afflicted with solid tumors which comprises systemically injecting into said mammal at a site distal from the solid tumor an amount of IL-4 effective for such treating.

The present invention also provides a method of inhibiting the growth of solid tumors in a mammal afflicted with solid tumors which comprises systemically injecting to mammal at a site distal from the solid tumor an amount of IL-4 effective for such inhibiting.

The present invention still further provides a method of inducing an effective immune response to inhibit a solid tumor growth or effect solid tumor regression in a mammal afflicted with solid tumors which comprises systemically injecting into a said mammal at site distal from the solid tumor an amount of IL-4 effective for such inducing.

The present invention also provides a method of augmenting an effective immune response to effect inhibition or regression of solid tumor growth in a mammal afflicted with solid tumors wherein immune response by said mammal in the absence of IL-4 is not strong enough or fast enough to effect tumor growth inhibition or solid tumor regression which comprises systemically injection into said mammal at a site distal to the solid tumor an amount of IL-4 effective for such augmenting.

The present invention also provides pharmaceutical compositions for inhibiting the growth of solid tumors or treating solid tumors or inducing an effective immune response to inhibit the growth of solid tumors in a mammal afflicted with solid tumors or augmenting an effective immune response to effect inhibition or regression of solid tumor growth in a mammal afflicted with solid tumors wherein immune response by said mammal in the absence of IL-4 is not strong enough or fast enough to effect tumor growth inhibition or solid tumor regression which comprises an amount of IL-4 effective for such purposes and a pharmaceutically acceptable carrier.

The present invention also provides the use of IL-4 for the manufacture of a medicament for treating solid tumors in mammals afflicted with solid tumors by systemic injection of IL-4 into such mammals at sites distal from the solid tumors.

DETAIL DESCRIPTION OF THE INVENTION AND OF THE PREFERRED EMBODIMENTS

Figure 1A:
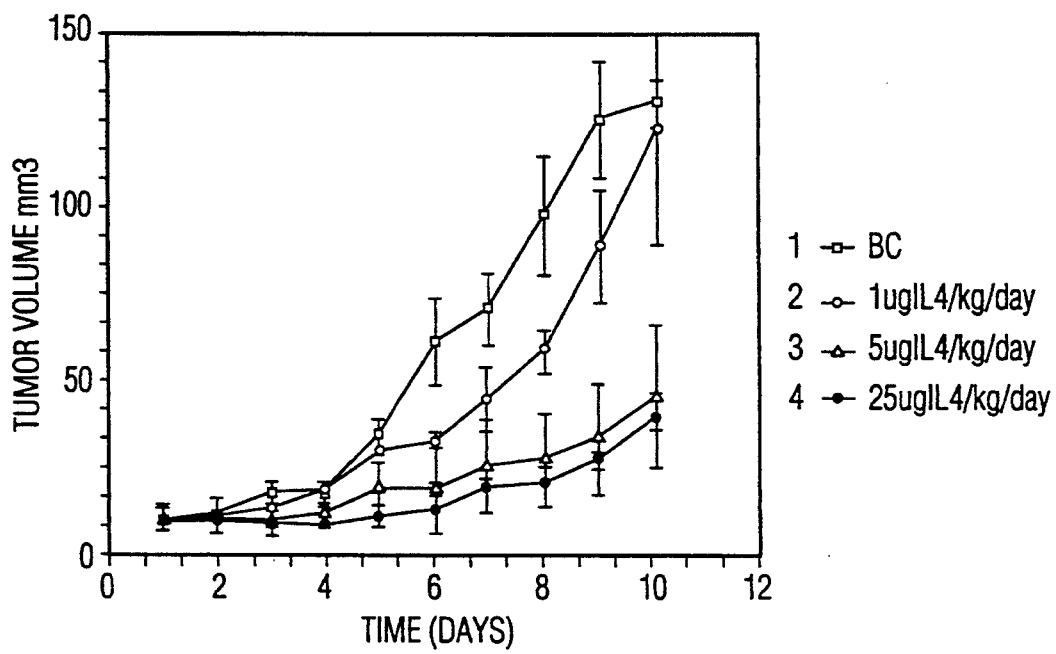
FIGS. 1A–1C illustrate solid tumor growth inhibition achieved by intraperitoneal administration of touring IL-4 in an athymic mouse model bearing S180 sarcomas (FIG. 1A), B16 melanomas (FIG. 1B) and Lewis lung carcinoma (FIG. 1C) in accordance with this invention.

We have surprisingly discovered that systemic injections of murine IL-4 administered to solid tumor bearing mice at a site distal from the solid tumor inhibits the growth of such solid tumors by modulating the immune response to tumor growth. These results contrast to the Tepper et al disclosure that murine IL-4 acts in an autocrine/paracrine manner to inhibit local tumor growth, i.e. at the tumor site, but does not inhibit solid tumor growth when administered at a distal site from the tumor. We have demonstrated such anti-solid tumor growth in an in vivo murine model using two epithelial tumors (Lewis lung carcinoma and B 16 melanoma) and a connective tissue tumor (S 180 sarcoma). Our data show that solid tumor regression occurs in immune competent mammals and solid tumor growth inhibition occurs in cytotoxic T cell deficient athymic animals. Our data indicate that systemic injections of IL-4 into solid tumor bearing mammals in accordance with our invention stimulates components of the immune system to effect anti-solid tumor response by IL-4 alone or in concert with the mammal's immune system. Thus, our data predict host-mediated anti-solid tumor effects by systemic administration of IL-4 would occur in any solid tumor type in which augmentation of an immune response would be beneficial.

The term "solid tumor" as used herein means any IL-4 sensitive solid tumor of the epithelial type (e.g. melanomas and lung carcinomas) as well as a connective tissue type solid tumor (e.g. sarcoma) and includes, but is not limited to all melanomas, renal cell carcinomas, breast carcinomas, lung carcinomas, lymphomas, myelomas, basal cell carcinomas, and colorectal carcinomas.

The phrase "treating solid tumors" as used herein means a broad range of anti-tumor responses resulting from systemic injection of IL-4 in accordance with this invention including: (1) effecting solid tumor regression; (2) inhibiting solid tumor growth; (3) inducing an effective immune reponse to inhibit tumor growth or effect solid tumor regression; and (4) augmenting an effective immune response to effect inhibition or regression of solid tumor growth in mammals. The immune response of the mammals in the absence of systemically administered IL-4 is not strong enough or fast enough to effect solid tumor growth inhibition or solid tumor regression but we have found effective methods which comprise systemically administering to solid tumor-bearing mammals an amount of IL-4, preferably recombinant IL-4 effective for each of such purposes.

The term "distal" used in the phrase "site distal from the solid tumors" to describe the injection site for IL-4 means a distance from the solid tumor beyond which soluble factors normally do not diffuse. Such a distance is also greater than the distance of drainage from a lymph node or the normal migration distance of human lymphocytes through tissue. The exact location for injection of IL4 at a site distal from the solid tumor will be chosen by the attending clinician after examination of the solid tumor(s) in the patient to be treated in accordance with this invention. Typically a site distal from a solid tumor in for example the left groin will be in a subcutaneous or intramuscular site on the arm or buttocks as opposed to around a left tumor-draining inguinal lymph node as disclosed by Forni, et al., in *Int. J. Can. Sup.* (1989) Vol. 4, 62–65 at p63.

The term "soluble factors" means any compound or substance in solution and includes factors such as IL-4, IFN-α, GM-CSF as well as drugs.

Any suitable IL-4 may be employed in the present invention. Complementary DNAs (cDNAs) for IL-4 have recently been cloned and sequenced by a number of laboratories, e.g. Yokoto et al., *Proc. Natl. Acad. Sci. USA*, (1986) Vol. 83:5894–5898 (human); Lee et al., Proc. Natl. Acad. Sci. USA, (1986) Vol. 83:2061–2065 (mouse); Noma et al., Nature (1986) Vol. 319:640–646 (mouse); and Genzyme Corporation, Boston, Mass. (human and mouse). Moreover, non-recombinant IL-4 has been purified from various culture supernatants, e.g. Sanderson et al., Proc. Natl. Acad. Sci. USA. (1986) Vol. 83:437–440 (mouse); Grabstein et al., J. Exp. Med., (1985) Vol. 163: 1405–1413 (mouse); Ohara et al., J. Immunol., (1985) Vol. 135: 2518–2523 (mouse BSF-1); Butler et al., J. Immunol. 133: (1984) Vol. 251–255 (human BCGF); and Farrar et al., J. Immunol., (1983) Vol. 131: 1838–1842 (mouse BCGF). The disclosures of all the above articles are incorporated herein by reference for their teachings of DNA and amino acid sequences and of methods of obtaining suitable IL-4 materials for use in the present invention.

Preferably, the IL4 used in the present invention is human IL-4, and most preferably it is the human version with the sequence described in Yoketo et al., Proc. Natl. Acad. Sci. USA (1986), Vol 83: 5894–5898 and PCT Patent Application No. 87/02990 published May 21, 1987 that is expressed in and isolated from E. coli (U.S. patent application No. 079,666, filed Jul. 29, 1987 now abandoned and U.S. patent application No. 194,799, filed Jul. 12, 1988now U.S. Pat. No. 4,958,007). The production of IL-4 from CHO cells is described in commonly-owned U.S. patent application Ser. No. 386,937, filed Jul. 28, 1989. The production of IL-4 from E. coli is described in commonly-owned U.S. patent application Ser. No. 429,588, filed Oct. 31, 1989. The disclosures of the above article, PCT application and U.S. patent applications are hereby incorporated herein by reference.

According to this invention, mammals are administered an effective amount of an IL-4 to inhibit solid tumor cell growth, to effect solid tumor regression, to induce an effective immune response, to inhibit solid tumor cell growth or to effect solid tumor regression or to augment an effective immune response to effect solid tumor growth inhibition or solid tumor regression. From about 0.25 to about 15 micrograms of IL-4, preferably human IL-4 ("hIL-4") recombinantly. produced from E. coli or CHO cells, more preferably E. coli-derived recombinant hIL-4, per kilogram of body weight per day is preferably administered. More preferably, mammals are administered about 5 to about 15 micrograms of recombinant hIL4 per kilogram of body weight per day, and most preferably mammals are administered about 5 to about 10 micrograms of recombinant hIL-4 per kilogram of body weight per day.

The amount, frequency and period of administration will vary depending upon factors such as the level of the neutrophil and monocyte count (e.g., the severity of the monocytopenia or granulocytopenia), age of the patient, nutrition, etc. Usually, the administration of IL-4 will be daily initially and it may continue periodically during the patient's lifetime. Dosage amount and frequency may be determined during initial screenings of neutrophil count and the magnitude of the effect of IL-4 upon the increase in antibody levels.

Administration of the dose can be intravenous, parenteral, subcutaneous, intramuscular, or any other acceptable systemic method. The IL-4 can be administered in any number of conventional dosage forms. Parenteral preparations include sterile solutions or suspensions. Dosages of more than about 10 to about 15 micrograms of recombinant IL-4 per kilogram of body weight are preferably intravenously administered to human beings.

The formulations of pharmaceutical compositions contemplated by the above dosage forms can be prepared with conventional pharmaceutically acceptable excipients and additives, using conventional techniques.

Presently, the IL-4 is preferably administered systemically via injection, preferably via subcutaneous or intraperitoneal injection or even intravenous injection at a site distal from the solid tumor. The solutions to be administered may be reconstituted lyophilized powders and they may additionally contain preservatives, buffers, dispersants, etc.

Preferably, IL-4 is reconstituted with 10 millimolar citrate buffer and preservative-free sterile water with the maximum concentration not to exceed 100 micrograms per milliliter and administered systemically via subcutaneous injection, intraperitoneal injection or via continuous intravenous infusion or by intravenous injection. For continuous infusion, the daily dose can be added to 5 ml of normal saline and the solution infused by mechanical pump or by gravity.

The effect of IL-4 on solid tumors in mammals can be determined inter alia by the reduction in tumor volume (which can be measured using standard techniques such as call per measurements, X-ray and MRI) as well as by increased life span or survival of such mammals by the following test protocol.

MATERIALS AND METHODS:

Mice. 10-wk-old female athymic mice (Harlan Sprague Dawley), 10-wk-old female Nu/Nu Balb/c mice (Charles River), 10-wk-old C57Bl/6 mice and 10-wk-old CD1 mice (Charles River) were obtained and housed in the VAF unit at the Schering-Plough Research facility located in Bloomfield, N.J.

Cell Cultures. The B16 melanoma and Lewis lung carcinoma (ATCC #CRL 1642) are tumor cell lines that arose spontaneously in C57Bl/6 mice. They share identical major histocompatibility antigens. The S180 sarcoma(ATCC#TIB66)is a cell line derived from sarcoma 180 ascites in Swiss Webster mice. The tumor cell lines were cultured in Dulbecco's minimal essential medium supplemented with 10% fetal bovine serum, 2 mM L-glutamine, 50 units/ml penicillin, 50 ug/ml stretomycin, Eagle minimum essential medium, vitamins and nonessential amino acids.

Cytokine, Murine rIL-4 0.064mg/mi($6 \times 10^7$U/mg) and human rIL-4 0.75 mg/ml ($1 \times 10^7$U/mg) obtained from Schering-Plough Corporation (Union, N.J.) were used at the indicated concentrations.

Animal Studies. Tumor cells at a concentration of $2 \times 10^6$ cells/0.2 ml were injected subcutaneously along the midline of the peritoneal cavity. Tumor volumes were estimated as the product of 3-dimensional caliper measurements. The IL-4 was administered daily either intraperitoneally or intravenously at the indicated dosage. For experiments involving antibody administration, a monoclonal antibody cell line secreting 11 B11 (antiIL-4), or a control monoclonal antibody cell line secreting the same isotype GL113 (anti-$\beta$Gal) was entrapped in alginate and injected intraperitoneally. By the fifth day after injecting the alginate-entrapped monoclonal cell line, the serum level of monoclonal antibodies detected was 15 ug/ml. The circulating levels of antibodies remained at this level for three weeks.

Chromium release assay. The method described by S. Gillis and K. A. Smith in J. Exp Med: (1977) Vol. 146, 468 was used. B16 melanoma cells ($2 \times 10^6$) were injected into the peritoneum of athymic or C57Bl/6 mice.

Murine IL-4 or buffer control was administered subcutaneously for the indicated time. Cytotoxic effector cells for these mice were harvested by tapping the peritoneal cavity. Target cells, B16 melanoma or Lewis lung carcinoma cells, were radiolabelled by incubating :$10^7$ cells/ml with 100 uCi $Na_2{}^{51}CrO_4$ (obtained from New England Nuclear) for 1 hour at 37° in 5% $CO_2$. The target cells were washed and incubated in 50 ml complete medium for 1 hour before being added to the assay. The effector (E) and target (T) cells were cultured together at E/T ratios of 20:1, 10:1,5:1,2.5:1 in triplicate wells of 96-well plates. After gently pelleting the cells together by centrifugation at 200 g for 3 minutes, the plates were incubated at 37° in 5%$CO_2$. Each experimental well contained. $5 \times 10^4$ target cells in 100 ul of complete medium. After 4 hours the plates were centrifuged to pellet the cells, and half of the supernatant was collected and counted in an LKB 1272 gamma counter. Spontaneous release of $^{51}Cr$ was determined from wells containing target cells alone in complete medium, and maximum release from wells containing target cells incubated in 1% Triton-X100.

$$\% \text{ Specific Cytotoxicity} = \frac{\text{experimental cpm* } - \text{ background release cpm} \times 100\%}{\text{total release cpm } - \text{ background release cpm}}$$

*CPM = counts per minute

Histologic Analysis. Tissue at the site of the tumor cell inoculation was fixed and embedded in paraffin, sectioned at 5 μm, and stained with either hematoxylin and eosin or Luxol fast blue for detection of eosinophils.

Results

Figure 1B:
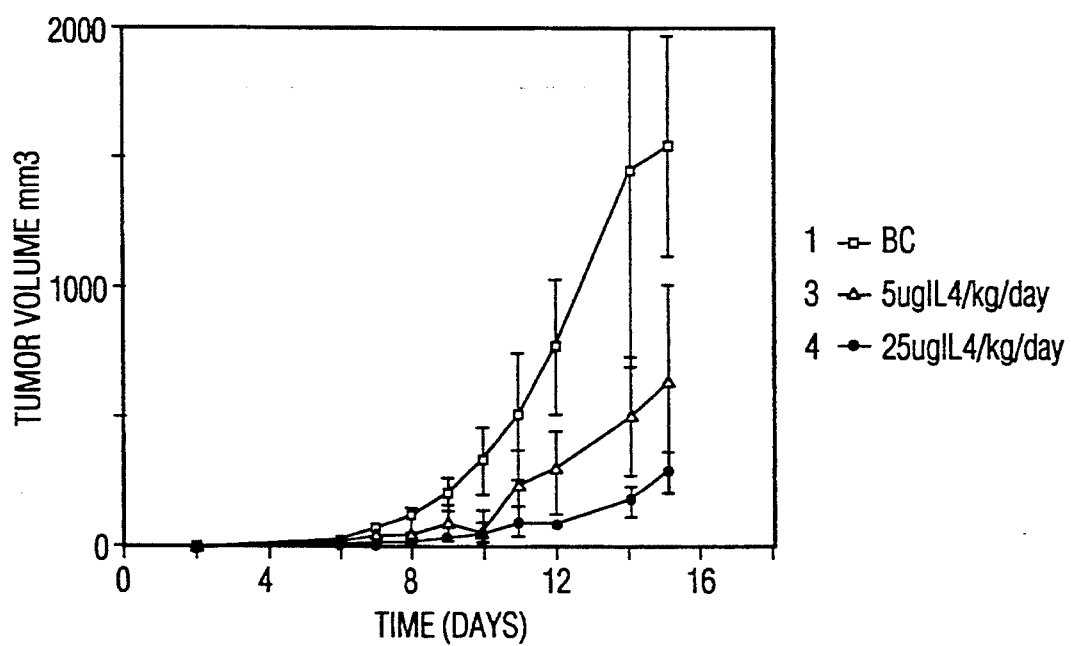
Figure 1C:
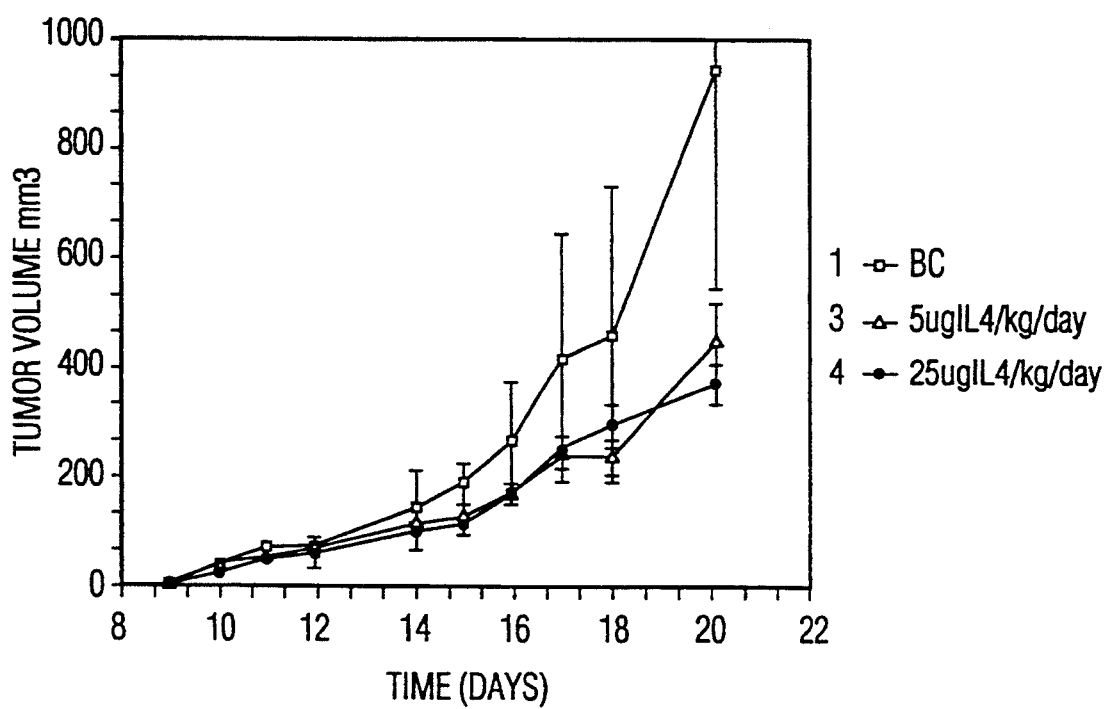

We initially evaluated the ability of murine IL-4 to affect the growth of several different tumor types at a distal site in athymic mice. Subcutaneous tumor growth in athymic mice was inhibited by murine IL-4 administered intraperitoneally compared to such mice receiving buffered control (BC). Dosage of 5 and 25ug/kg/day caused statistically significant (p<0.05)inhibition of B16 melanoma, S180 sarcoma and Lewis lung carcinoma growth as shown in FIG. 1. One set of experiments showed that the statistically significant inhibition of tumor growth of B16 melanoma and Lewis lung carcinoma seen with murine IL-4 treatment (25ug/kg/day) could be abolished by administering the anti-IL-4 secreting cell line. Murine and human IL-4 are species-specific with respect to receptor binding. See for example L. S. Park et al. *J, Exp. Med.,* (1987) Vol 166, 476–480; J. Ohara et al., *Nature,* (1987) Vol. 325, 537–540; and K. Nakajima et al., *J. Immuno.,* (1987) Vol. 139,774–779. Human IL-4 administered intraperitoneally at 25 ug/kg/day had no detectable effect on the subcutaneous growth of B16 melanoma or Lewis lung carcinoma in athymic nude mice (data not shown). This suggests a species-specific antitumor activity associated with IL-4.

In order to determine if one possible mechanism of action of murine IL-4 was a direct inhibitory affect on tumor growth in vivo, the degree of proliferation of tumor cells was monitored in the presence and absence of murine IL-4. In vitro proliferation of the tumor cells used in these experiments was not affected by murine IL-4. As assessed by $^3$H-thymidine incorporation or by enumeration of tumor cell numbers, concentrations of murine IL-4 as high as 25 ug/ml had not direct detectable effect on the proliferation of B16 melanoma, S180 sarcoma of Lewis lung carcinoma (data not shown).

Figure 2A:
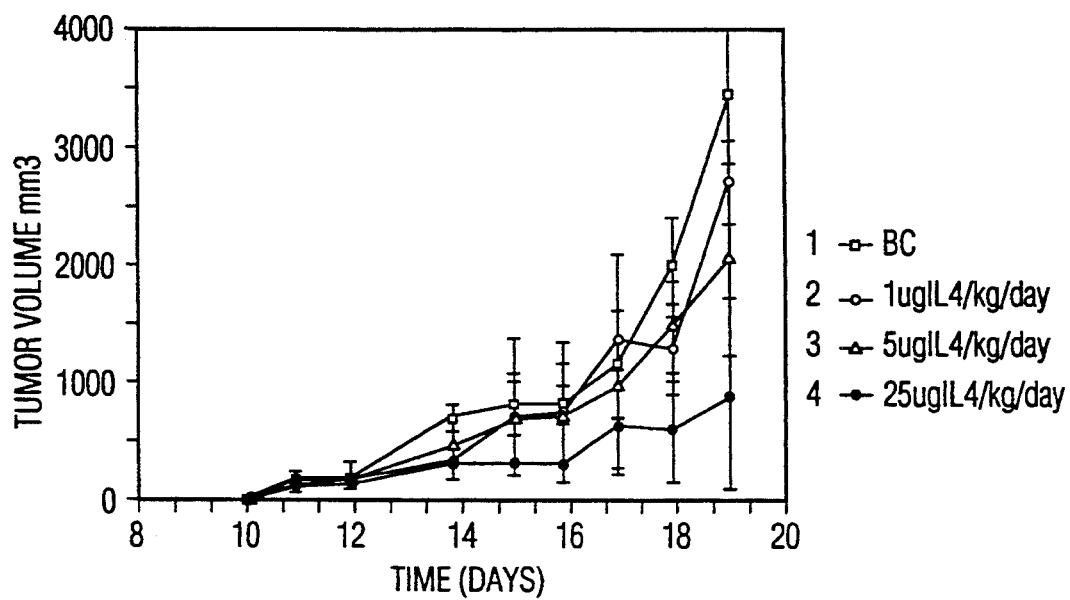
FIGS. 2A and 2B illustrate solid tumor-growth inhibition achieved by intraperitoneal injection of murine IU4 in a syngeneric C57Bl1/6 mouse model bearing B16 tumors (FIG. 2A) and Lewis lung carcinomas (FIG. 2B)in accordance with this invention.
Figure 2B:
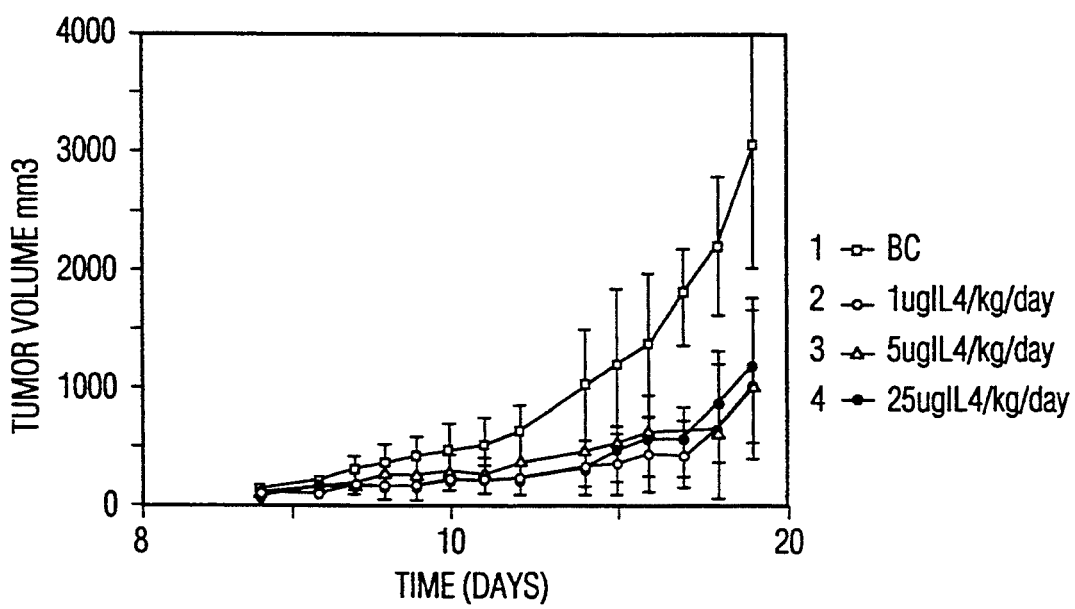

The effect of intraperitoneal administration of murine IL-4 on subcutaneous tumor growth in a syngeneic host was examined using B16 melanoma and Lewis lung carcinoma in C57Bl/6 mice. As shown in FIGS. 2 A & B, dosages as low as 1 ug/kg/day caused significant inhibition of Lewis lung carcinoma growth after 12 days of treatment (FIG. 2A) while significant inhibition of B16 melanoma growth occurred after 15 days of treatment with murine IL-4 at 25 ug/kg/day (FIG. 2B). The growth rate of both these tumors was slower in IL-4 treated animals compared to tumors in animals receiving buffered control (BC).

Figure 3:
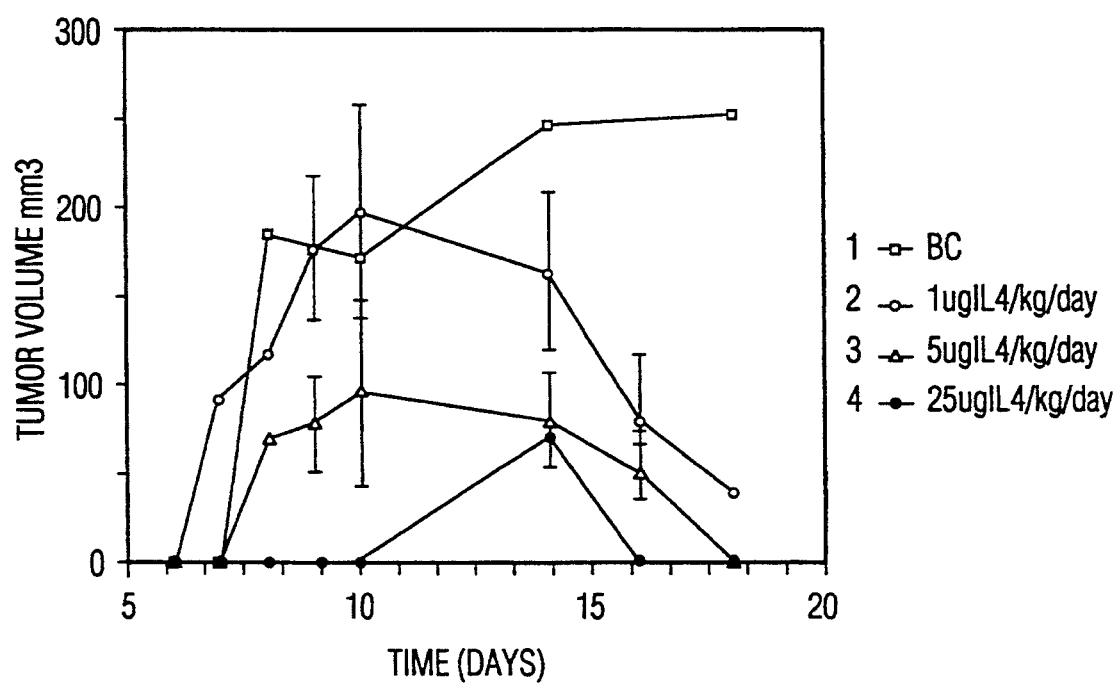
FIGS. 3 illustrates the solid tumor regression and solid tumor growth inhibition achived by intraperitoneal administration of IU4 to allogeneic CD1 mice bearing $180 sarcomas in accordance with this invention.

Subcutaneous tumor growth in an allogeneic host was affected by intraperitoneal administration of murine IL-4. Both inhibition and regression of S180 tumors in CD1 mice occurred over the dosage range of 1 to 25 ug/kg/day as shown in FIG. 3. In the buffer control-treated tumor-bearing animals no regression of the tumor occurrs. However, the rate of increased tumor growth seems to be leveling off.

Figure 4:
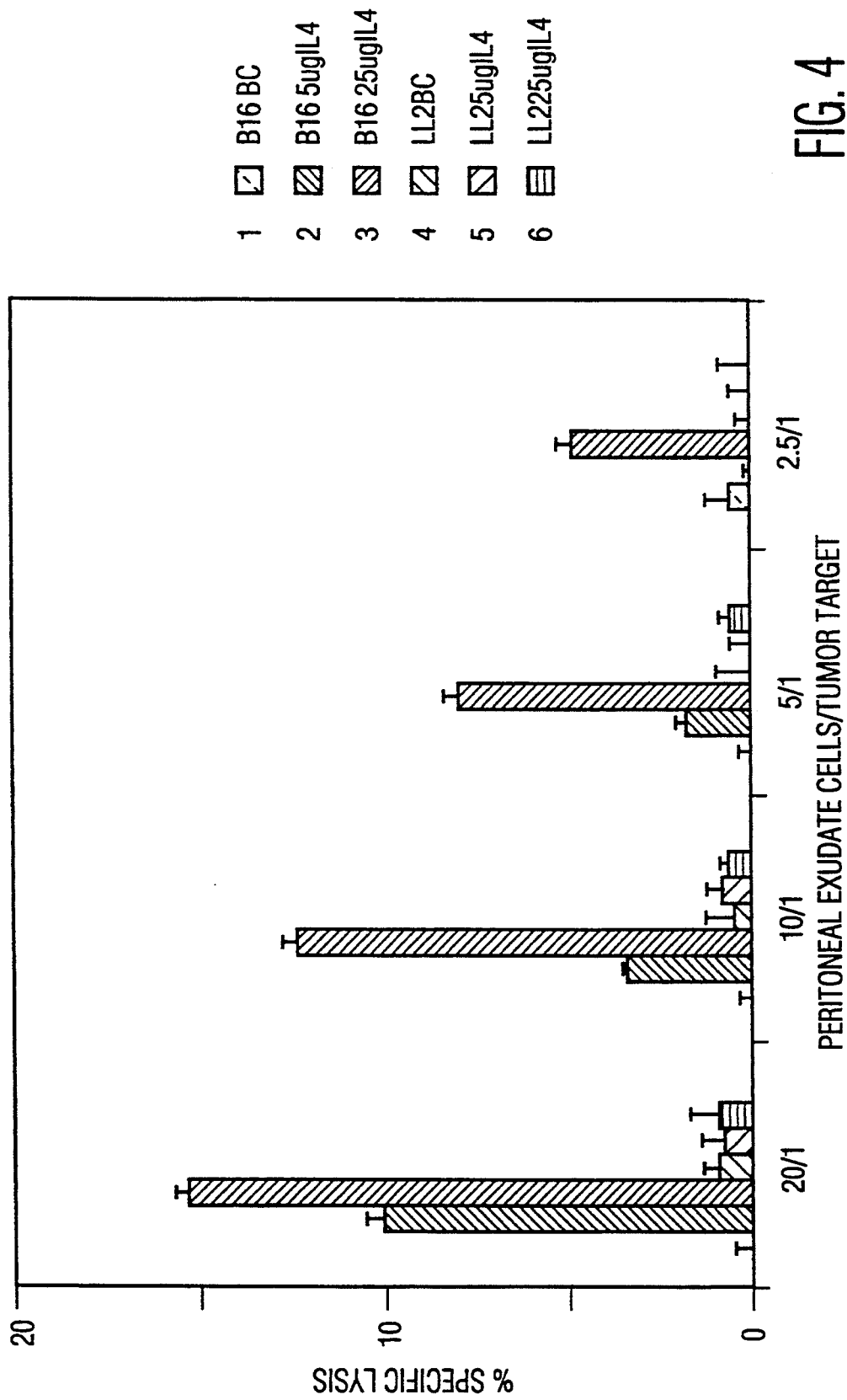
FIG. 4 illustrates the effect of systemic administration of murine IL-4 to enhance the murine immune system to inhibit specific tumor growth.

When peritoneal cells were gathered from a tumor-bearing animal that was injected with murine IL-4 at a site distal to the tumor, the peritoneal cells showed selective cytotoxicity toward cells from the same tumor cell line. As shown in FIG. 4, subcutaneous administration of murine IL-4 to C57Bl/6 mice bearing peritoneal B16 melanoma tumors enabled peritoneal cells from these animals to cause $^{51}Cr$ release from B16 melanoma cells, but did not increase their cytotoxicity toward Lewis lung carcinoma cells. Pertioneal cells from buffer control-treated animals bearing B16 melanomas were unable to lyse either tumor target. These data demonstrate that murine IL-4 enhances the ability of the murine immune system to inhibit specific tumor growth. These data also predict that human IL-4, preferably recombinant IL-4 would have clinical application in humans for the treatment of solid tumor since the growth of both epithelical-type tumors (melanomas and lung carcinomas) and a connective tissue type tumor (sarcoma) were inhibited. Futhermore, the inhibition of tumor growth by systemic injection of murine IL-4 into allogeneric murine hosts in accordance with this invention predicts that normal immune reactions in mammals afflicted with solid tumors would be enhanced by systemic administration of IL-4 in accordance with this invention.

What is claimed is:

1. A method of treating solid tumors in a mammal afflicted with solid tumors which comprises systemically injecting into said mammal at a site distal from the solid tumors an amount of IL-4 effective for such treating.

2. A method of claim 1 wherein treating solid tumors comprises (1) effecting solid tumor regression; (2) inhibiting solid tumor growth; (3) inducing an effective immune response to inhibit tumor growth or effect solid tumor regression; or (4) augmenting an effective immune response to effect inhibition or regression of solid tumor growth in mammals wherein the immune response of the mammals in the absence of systemically administered IL-4 is not strong enough or fast enough to effect solid tumor growth inhibition or solid tumor regression.

3. The of claim 1 wherein human IL-4 is administered.

4. The method of claim 1 wherein *E. coli*-derived recombinant human IL-4 is administered.

5. The method of claim 1 wherein the amount of IL-4 administered is in the range of about 0.25 to about micrograms per kilogram of body weight per dose.

6. The method of claim 1 wherein the solid tumors are epithelial tumors selected from the group consisting of all melanomas, renal cell carcinomas, breast carcinomas, lung carcinomas, lymphomas, myelomas, basal cell carcinomas and colorectal carcinoma.

7. A method of treating non-small cell lung carcinomas in a mammal afflicted with such carcinomas which comprises systemically injecting into said mammal at a site distal from the non-small cell lung carcinomas an amount of IL-4 effective for such treatment.

8. The method of claim 7 wherein IL-4 is administered subcutaneously.

9. The method of claim 7 wherein IL-4 in the amount of about 0.25–1 micrograms per kilogram of body weight is administered three times a week or daily.

* * * * *